US009456913B2

(12) United States Patent
Melsheimer

(10) Patent No.: US 9,456,913 B2
(45) Date of Patent: Oct. 4, 2016

(54) IMPLANT INTRODUCER WITH HELICAL TRIGGER WIRE

(71) Applicant: Cook Medical Technologies LLC, Bloomington, IN (US)

(72) Inventor: Jeffry Scott Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 173 days.

(21) Appl. No.: 14/206,905

(22) Filed: Mar. 12, 2014

(65) Prior Publication Data

US 2014/0277350 A1 Sep. 18, 2014

Related U.S. Application Data

(60) Provisional application No. 61/793,050, filed on Mar. 15, 2013.

(51) Int. Cl.
*A61F 2/962* (2013.01)
*A61F 2/95* (2013.01)

(52) U.S. Cl.
CPC ........ *A61F 2/962* (2013.01); *A61F 2002/9511* (2013.01); *A61F 2230/0065* (2013.01); *A61F 2230/0091* (2013.01)

(58) Field of Classification Search
CPC ............ A61F 2/95; A61F 2/07; A61F 2/962; A61F 2230/0091; A61F 2230/00655; A61F 2230/0069; A61F 2002/30579; A61F 2002/30785; A61F 2002/30062; A61F 2002/30504; A61F 2310/00293; A61F 2/2427; A61F 2/243; A61F 2/2436; A61F 2/2439; A61F 2002/011; A61F 2002/9528; A61F 2002/9534; A61F 2002/952; A61F 2/966; A61F 2002/9505; A61F 2002/9511; A61F 2002/9665; A61B 17/12118
USPC ........................ 623/1.11, 1.13, 1.23; 606/200
See application file for complete search history.

(56) References Cited

U.S. PATENT DOCUMENTS

| | | | |
|---|---|---|---|
| 4,878,906 A * | 11/1989 | Lindemann | A61F 2/91 606/108 |
| 5,556,414 A | 9/1996 | Turi | |
| 5,569,197 A * | 10/1996 | Helmus | A61M 25/09 604/102.02 |
| 6,245,100 B1 * | 6/2001 | Davila | A61F 2/07 606/198 |
| 7,279,208 B1 | 10/2007 | Goffena et al. | |
| 7,722,657 B2 | 5/2010 | Hartley | |
| 8,303,616 B2 | 11/2012 | Abrams et al. | |
| 8,366,699 B2 | 2/2013 | Jimenez et al. | |
| 2003/0233140 A1 | 12/2003 | Hartley et al. | |
| 2004/0193254 A1 | 9/2004 | Greenberg et al. | |
| 2005/0090893 A1 | 4/2005 | Kavteladze et al. | |
| 2007/0016281 A1 * | 1/2007 | Melsheimer | A61F 2/95 623/1.11 |
| 2008/0027529 A1 | 1/2008 | Hartley et al. | |
| 2010/0274340 A1 | 10/2010 | Hartley et al. | |

(Continued)

*Primary Examiner* — David C Eastwood
*Assistant Examiner* — Mikail Mannan
(74) *Attorney, Agent, or Firm* — Brinks Gilson & Lione; Ryan L. Marshall

(57) ABSTRACT

A delivery device for deploying an expandable, endoluminal prosthesis within a body vessel is disclosed. The delivery device may include one or more stent graft retention scaffolds having a plurality of arches, each arch encompassing an aperture forming a helical path and a trigger wire passing through at least two of the apertures following the helical path, wherein at least a portion of the stent graft is retained in a compressed configuration on the delivery device by the retention scaffold and trigger wire.

15 Claims, 7 Drawing Sheets

(56) References Cited

U.S. PATENT DOCUMENTS

| | | |
|---|---|---|
| 2011/0054585 A1 | 3/2011 | Osborne |
| 2011/0144735 A1 | 6/2011 | Hartley et al. |
| 2012/0172968 A1 | 7/2012 | Chuter et al. |
| 2012/0239130 A1 | 9/2012 | Hartley et al. |
| 2012/0290066 A1 | 11/2012 | Nabulsi et al. |

* cited by examiner

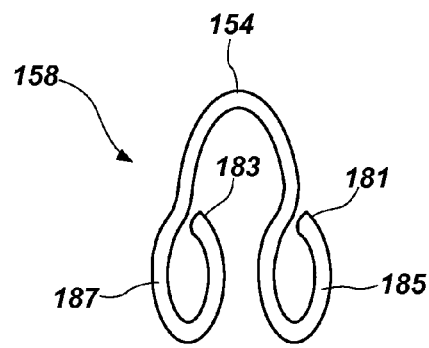
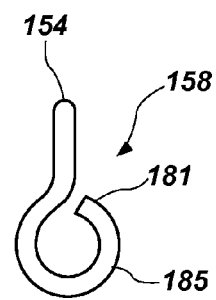
FIG. 5A
FIG. 5B
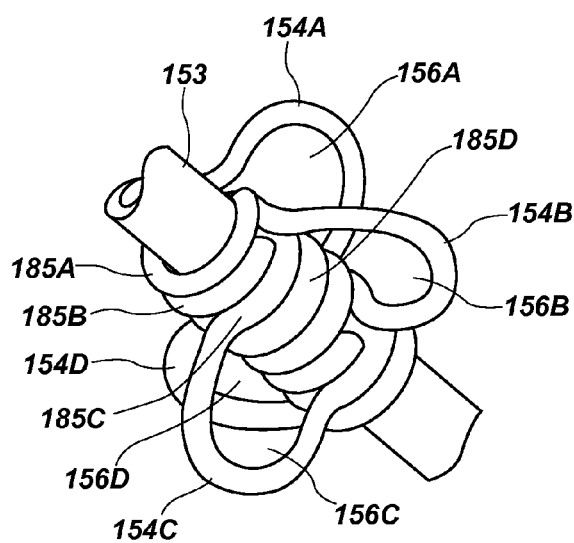
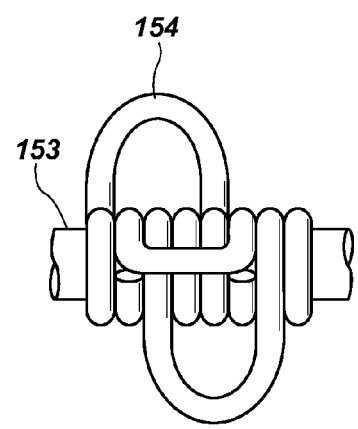
FIG. 6A
FIG. 6B

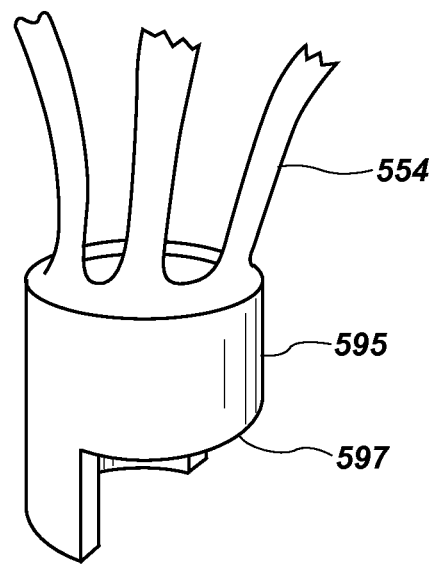
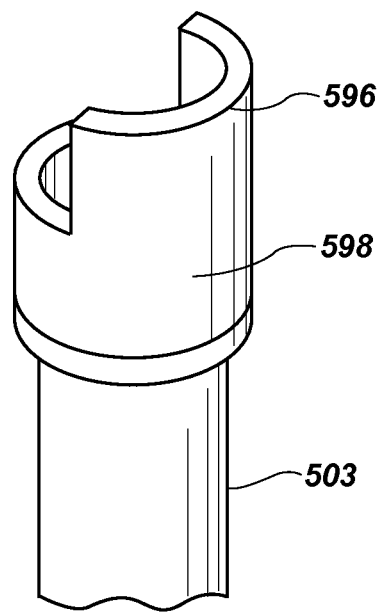
FIG. 10

IMPLANT INTRODUCER WITH HELICAL TRIGGER WIRE

CROSS-REFERENCE TO RELATED APPLICATIONS

This application claims the benefit of U.S. Provisional Application No. 61/793,050 filed Mar. 15, 2013, the entire contents of which are hereby incorporated by reference.

FIELD OF INVENTION

This disclosure relates generally to apparatus and methods for treating medical conditions. More specifically, this disclosure relates to apparatus and methods for deploying endoluminal prostheses in body vessels to treat those medical conditions.

BACKGROUND OF THE INVENTION

Endoluminal prostheses may be inserted into a body lumen such as an anatomical vessel or duct for various purposes. Prostheses may maintain or restore patency in a formerly blocked or constricted passageway, for example, following a balloon angioplasty procedure. Other prostheses may be used for different procedures. For example, a prosthesis may include one or more stents placed in or about a graft, and the stents may hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable. Some stents can have characteristics of both self-expanding and balloon-expandable stents. Self-expanding stents may be delivered to a target site in a compressed configuration and subsequently expanded by removing a delivery sheath, removing trigger wires, and/or releasing diameter reducing ties. A self-expanding stent expands primarily based on its own expansive force without the need for further mechanical expansion. A stent may be made of a shape-memory alloy such as nitinol. The shape-memory alloy may be employed to cause the stent to return to a predetermined configuration upon removal of a sheath or other device maintaining the stent in its predeployment configuration.

Deployment devices are used to deploy prostheses, particularly those including self-expanding stents, within various body lumens. In some deployment devices, trigger wires are used to restrain a prosthesis in a particular position on the deployment device or to restrain one or more self-expanding stents of the prosthesis in a compressed state. The trigger wires may releasably couple the proximal and/or distal ends of the prosthesis to the deployment device. Typically, one or more trigger wires are looped through a portion of a stent near a vertex of the stent. For example, trigger wires may be used to restrain a "Z-stent" or Gianturco stent having a series of substantially straight segments interconnected by a series of bent segments. The trigger wires may be disposed through, and pull upon, the bent segments to pull the stent closely against the deployment device.

In the region of the deployment device in which the prosthesis is carried, trigger wires can foul or catch with stent components on the prosthesis, particularly when the deployment device is bent to pass through convolutions in the anatomical vessel or duct. This may cause inaccurate deployment or even jamming or breakage of the trigger wire.

Trigger wires also may be used in conjunction with different stent designs such as cannula-cut stents having relatively acute or pointed bends. The designs of cannula-cut stents may facilitate compression of the stents to a relatively small delivery profile due to the tight bends of the apices. With such stents, the trigger wires may be looped around one or more vertices formed at the proximal and/or distal apices, e.g., a location where an individual apex splits into two separate strut segments.

If trigger wires are threaded through the vertices of such cannula-cut stents, the trigger wires may become crimped at the vertices during compression of the stents to a reduced diameter delivery profile. If the trigger wires are crimped between the strut segments, the trigger wires and/or strut segments may become damaged. Furthermore, when compressing cannula-cut stents having relatively acute bends to a significantly reduced radial profile, barbs disposed near the apices of the stents may become entangled with the stent struts and/or the trigger wires.

Typically, multiple trigger wires are threaded through multiple vertices of a stent to restrain the end of the stent in the reduced diameter delivery profile. Additional trigger wires may be added to more securely restrain the stent. However, such additional trigger wires may increase the retraction force that is required to release the stent. Such additional trigger wires also may increase the likelihood of one or more of the trigger wires becoming entangled with portions of the stent such as barbs.

Another issue that arises with the deployment of endoluminal prosthesis (also called implants) is the ability to selectively release the prosthesis, such as a supra-renal stent, to anchor the implant once its position has been established. Some conventional devices use multiple trigger wires which each release their respective "anchor-feature." Unfortunately, multiple trigger wires increase the cross-sectional area of the loaded introducer that is even more problematic in low profile and extra low profile devices. Such delivery devices are designed to reduce the packing space of the implant and may be compromised or function less desirably when having multiple trigger wires.

In view of the above, it would be desirable to provide an apparatus configured to release a stent with a reduced retraction force while also reducing the likelihood of entanglement and damage to the trigger wires and stent struts. It is also desirable to provide alternative options for deployment of prostheses and for controlling the retention and release of the prostheses including those with fenestrations.

SUMMARY OF THE INVENTION

The present embodiments provide an endoluminal prosthesis for implantation within a human or animal body for repair of damaged vessels, ducts, or other physiological pathways and systems and method for delivering such an endoluminal prosthesis.

In one aspect, an endovascular delivery device is disclosed. The device includes a central catheter; a stent graft circumferentially located about a portion of the central catheter, the stent graft comprising a tubular body of a biocompatible material with a lumen therethrough; a retention scaffold comprising a plurality of arches, each arch encompassing an aperture forming a helical path; a trigger wire passing through at least two of the apertures following the helical path, wherein at least a portion of the stent graft is retained in a compressed configuration on the delivery device by the retention scaffold and the trigger wire.

In another aspect, an endovascular delivery device is disclosed. The device includes a central catheter; a shaft; a stent graft circumferentially located about a portion of the central catheter, the stent graft comprising a tubular body of a biocompatible material with a lumen therethrough; a retention scaffold comprising a proximal end and a piloting end and a plurality of arches, each arch encompassing an aperture forming a helical path, wherein the piloting end is configured to form an interlock with the shaft for rotating or longitudinally displacing a portion of the retention scaffold, a trigger wire passing through at least two of the apertures following the helical path, wherein the stent graft is retained in a compressed configuration on the delivery device by the retention scaffold and the trigger wire.

In some embodiments, the stent graft comprises stent struts comprising openings and forming gaps between adjacent stent struts. In some embodiments, the arches extend through stent strut openings. In some embodiments, the arches extend through stent strut gaps. In some embodiments, the arches extend through stent strut openings and stent strut gaps.

In some embodiments, the arches are located circumferentially about the central catheter. In some embodiments, the arches are helically located about the central catheter. In some embodiments, the retention scaffold is integral with the central catheter. In some embodiments, the retention scaffold is located circumferentially on the central catheter. In some embodiments, the retention scaffold has distal and proximal ends and the arches bow radially outward when at least one of the distal or proximal ends moves longitudinally toward the other end.

In some embodiments, each arch is formed from a lateral strut having first and second ends, each of the ends forming a loop that is circumferentially located about the central catheter. In some embodiments, the retention scaffold comprises a sleeve having a plurality of slots wherein the slots are filled with cleats each associated with one of the arches. In some embodiments, the retention scaffold comprises a sleeve having a plurality of brackets radially mounted about the sleeve, and each bracket associated with least one of the arches.

In one aspect, a method of deploying a stent graft in a patient is disclosed. The method includes providing an endovascular delivery device, having: a central catheter; a stent graft circumferentially located about the central catheter comprising a tubular body of a biocompatible material with a lumen therethrough; a retention scaffold comprising a plurality of arches, each arch encompassing an aperture forming a helical path; a trigger wire passing through at least two of the apertures in the helical path, wherein the stent graft is retained in a compressed configuration on the delivery device by the retention scaffold and the trigger wire; and withdrawing the trigger wire through the apertures.

BRIEF DESCRIPTION OF THE DRAWINGS

FIG. 5A depicts a perspective view of one embodiment of the invention.

FIG. 5B depicts a side-profile view of the embodiment of FIG. 5A without a central catheter.

FIG. 6A depicts a perspective view of the embodiment in FIGS. 5A and 5B with a central catheter.

FIG. 6B depicts a top view of the embodiment shown in FIG. 6A with a central catheter.

FIG. 10 depicts a piloting component for use in various embodiments of the invention without a central catheter.

DETAILED DESCRIPTION

The present disclosure relates to apparatus and methods for preparing and deploying endoluminal prostheses in body vessels to treat various medical conditions.

In the present disclosure, the term "proximal" refers to a direction that is generally closest to the heart during a medical procedure, while the term "distal" refers to a direction that is farthest from the heart or other target tissue or organ during a medical procedure.

As used herein, the term "malecot" refers to a multi-winged configuration of arches of a cannula or catheter. The multi-winged configuration can radially contract or expand from longitudinal movement of one end of the cannula or catheter toward the other end.

As used herein, the term "trigger wire" refers to a slender filament of metal, usually circular in section, manufactured in a great variety of diameters and metals that restrain a portion of a prosthesis on a deployment device.

The invention will be discussed generally with respect to deployment of a stent graft into a blood vessel or lumen such as an aortic or and renal artery but is not so limited for use at any one particular area of a patient's anatomy. A wire guide is inserted into a patient's vasculature with an introducer needle using, for example, a percutaneous vascular access Seldinger technique.

Figure 1:
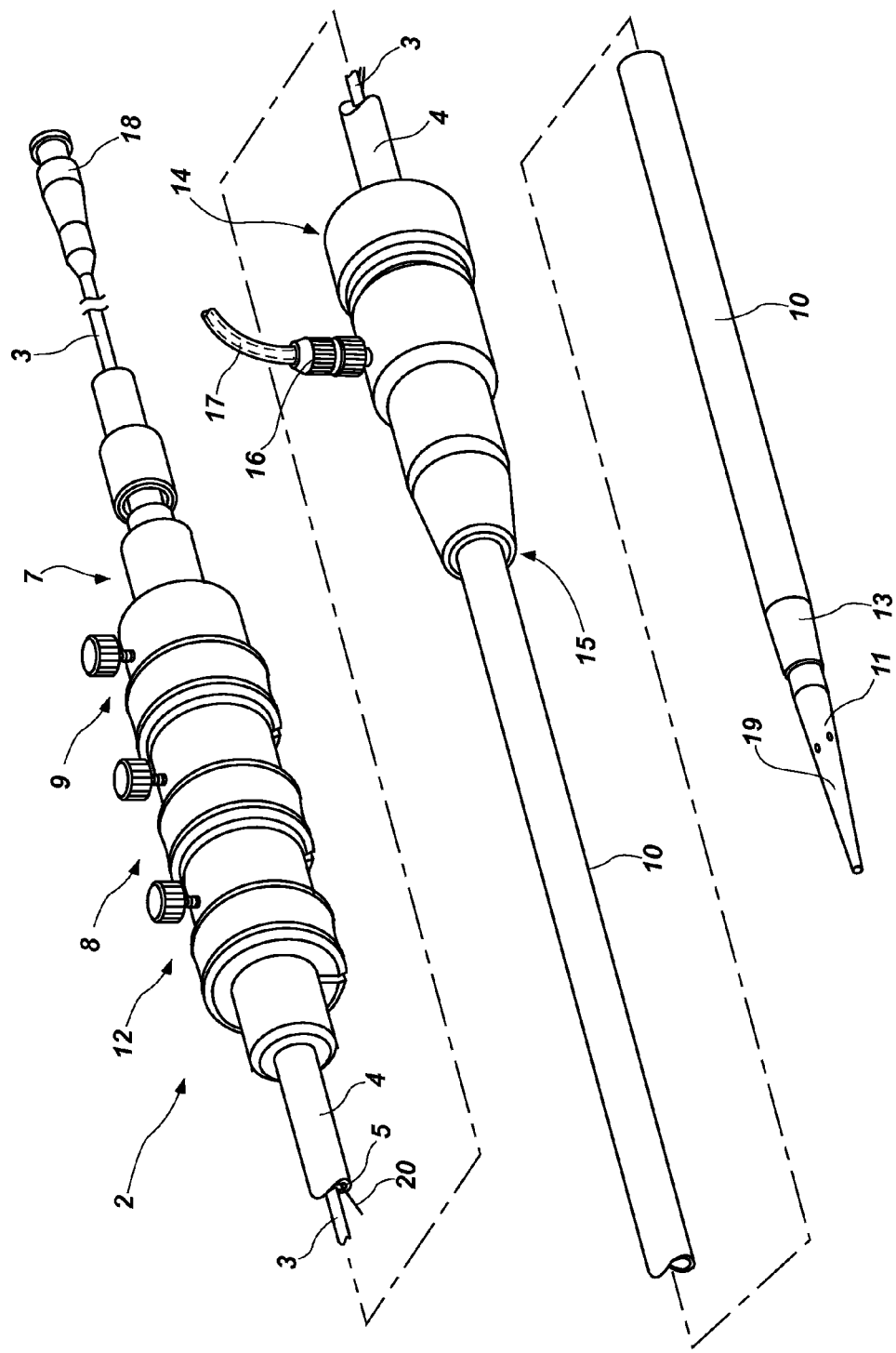
FIG. 1 depicts an introducer or delivery device according to one embodiment of the present invention.

FIG. 1 depicts a delivery device 2. The delivery device 2 has a central catheter 3. The central catheter may be configured as an elongate tubular member having a distal end, a proximal end, and a lumen extending longitudinally between the distal and proximal ends. The wire guide is passable through the central catheter 3—that is, the central catheter can pass over and along the previously introduced wire guide. In use, the distal end of the central catheter 3 may be adapted to remain outside of the body of the patient while the proximal end may be adapted for insertion into a body vessel of a patient. A male Luer lock connector hub 18 is provided at the distal end of the central catheter 3 in a handle 7 for connection to syringes and other medical apparatus. The distal end of the central catheter 3 extends from the handle 7 to a tapered nose cone dilator 11 through a lumen 5 of a delivery catheter 4.

Nose cone dilator 11 includes a tapered end 19 for accessing and dilating a vascular access site over the wire guide (not shown). The tapered nose cone dilator aids advancing the proximal end of the delivery device 2 within the body vessel. An introducer sheath 10 is disposed coaxially around the delivery catheter 4 and extends from a tapered end 13 to a connector valve and manipulator 14 secured to the distal end 15 of the introducer sheath 10. The introducer sheath 10 extends proximally to the nose cone dilator 11 and covers a stent graft 60 (not shown in FIG. 1). The stent graft is circumferentially located about a central catheter 3 and delivery catheter 4 and within the introducer sheath 10. The introducer sheath 10 is withdrawn to deliver the stent graft 60 when the deployment device is in a selected position within a patient's vasculature.

Connector valve 14 includes a silicone disk (not shown) for preventing the backflow of fluids therethrough and from the patient's vasculature as the delivery device is inserted and advanced through the vasculature. The disk includes a slit for the insertion of the nose cone dilator 11 and delivery catheter 4. Connector 14 also includes side arm 16 to which a tube 17 is connected for introducing and aspirating fluids therethrough. Thus, connector 14 may be configured to enable the introduction of liquids (e.g., contrast media or therapeutic agents) during a deployment procedure. In one example, an angiographic contrast fluid may be introduced into the connector. The contrast fluid may travel through the central catheter 3 to the nose cone dilator 11 where the contrast fluid may be ejected from one or more side ports in the nose cone dilator.

The handle 7 of the delivery catheter 4 may include one or more trigger wire release mechanisms such as 8, 9, and 12 shown in FIG. 1. The trigger wire release mechanisms are used to release various portions of the stent graft and are associated with respective trigger wires. As can be appreciated, the number of trigger wire release mechanisms can vary depending on the number of trigger wires utilized and the number of locations for sequential release of anchors in a given prosthesis.

The stent graft 60 is retained on the delivery device by the use of one or more trigger wires and one or more retention scaffolds (not shown in FIG. 1 but described in more detail below) until the trigger wires and sheath 10 are removed. For example, the proximal end of the stent graft may be retained by a retention scaffold and trigger wire until the trigger wire is removed by operation of release device 12. The distal end of the stent graft 60 can be retained on the delivery device by the use of an additional trigger wire (not shown) associated with the release device 8. In some embodiments, the presence of a second trigger wire is unnecessary in which case release device 8 is absent. The handle also can include a third release mechanism 12 for an optional trigger wire for further deployment (such as at a fenestration) of the stent graft 60 if so desired. In some embodiments, the presence of the trigger wire for longitudinal deployment may be omitted in which case the third release mechanism 12 is absent.

In some embodiments, a single trigger wire may be used for proximal, intermediate (such as at a fenestration point), and distal deployment of the stent graft.

The stent graft 60 can be retained on the delivery device 2 using a retention scaffold. The retention scaffold can take various forms as shown in FIGS. 2-10. In some embodiments, the retention scaffold may be located in a single position such as the initial anchoring point at one end of the stent graft. In some embodiments, the retention scaffold may also be located along the entire length of the stent. In some embodiments, more than one retention scaffold may be used so that a retention scaffold is located at each desired stent graft release point or anchoring site.

Figure 2:
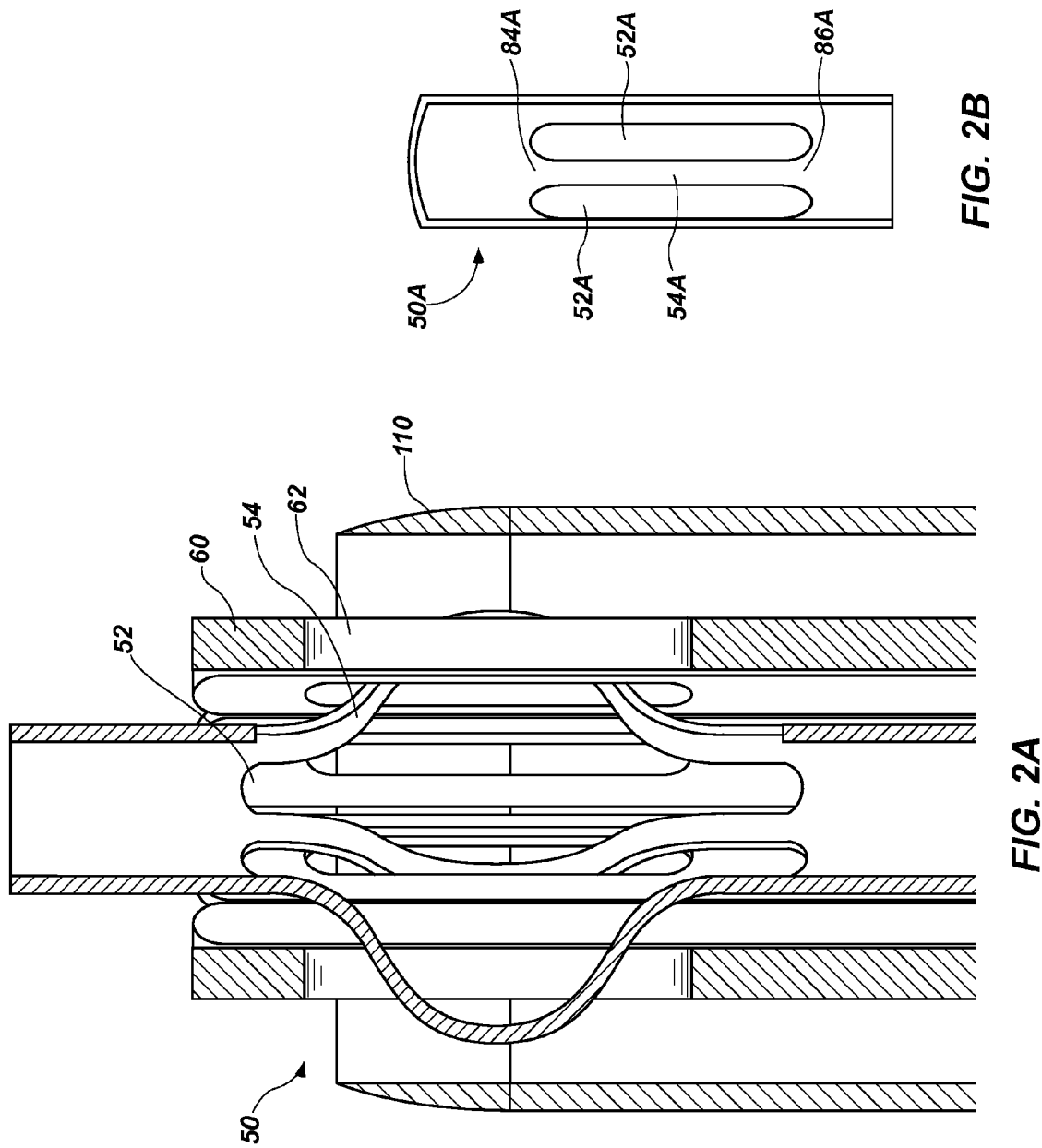
FIG. 2A depicts a cross sectional view of one embodiment of the invention in a form for retaining a stent graft.
FIG. 2B depicts a cross sectional view of the embodiment of the FIG. 2A in a form for loading a stent graft to be secured to a deployment device.
Figure 3:
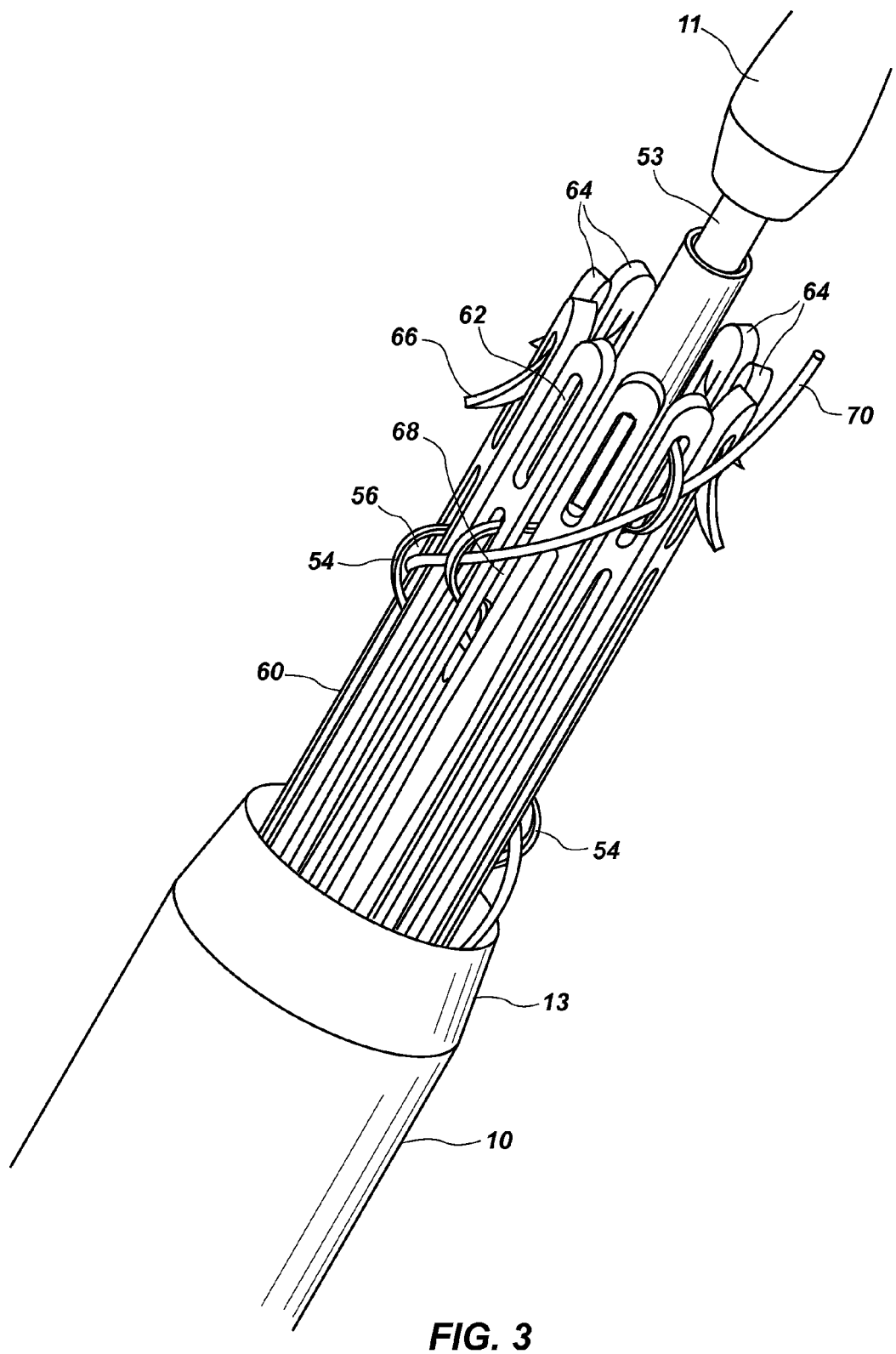
FIG. 3 depicts a perspective view of one embodiment of the invention with an introducer sheath partially withdrawn from the proximal end of a stent graft.
Figure 4:
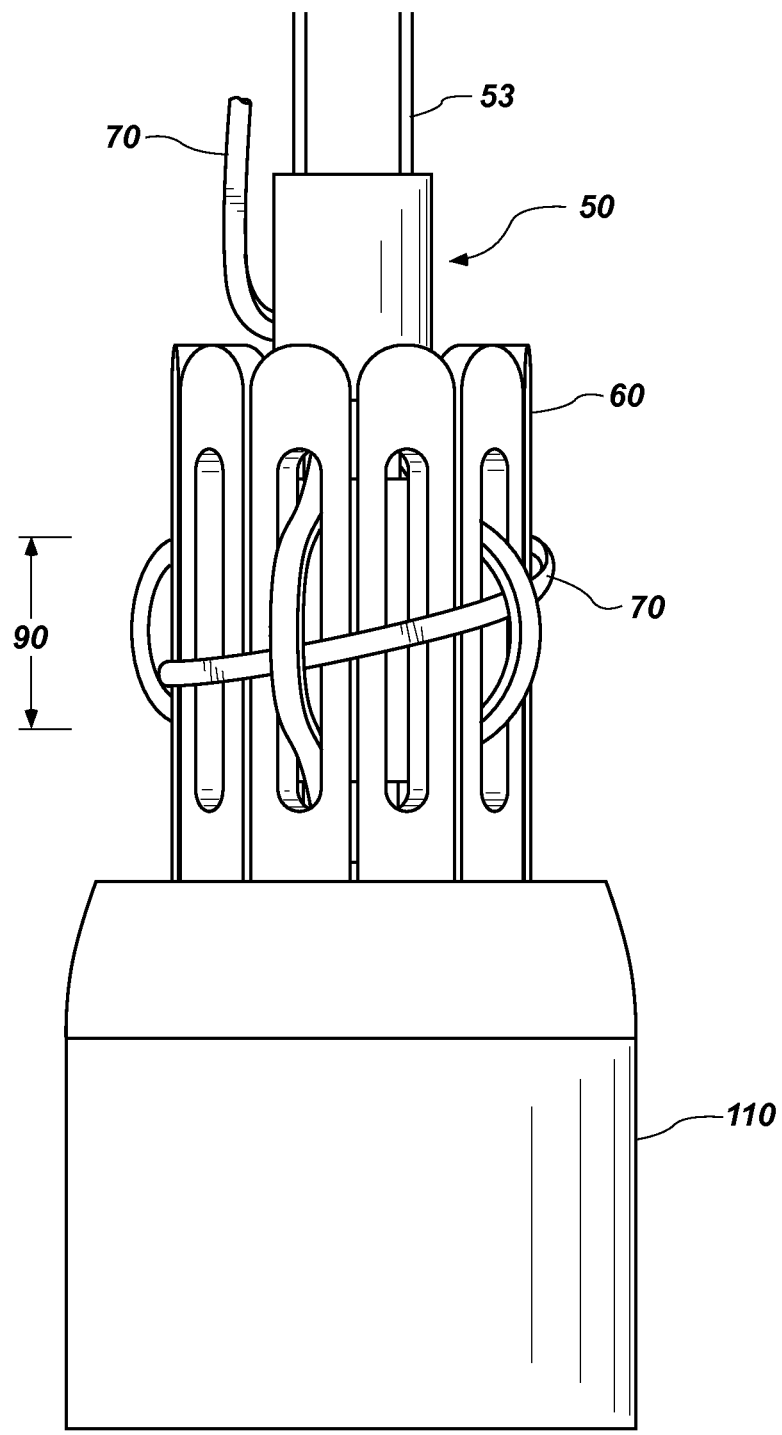
FIG. 4 depicts a perspective view of one embodiment of the invention.

Referring to FIGS. 2-4, a retention scaffold 50 passes over a central catheter 53 (not shown in FIGS. 2A and 2B). The retention scaffold 50 includes a plurality of slots 52 and a plurality of arches 54. In some embodiments, the plurality of slots and arches are circumferentially located about a common longitudinal location (see FIG. 2A for example). In other embodiments, the plurality of slots and arches are located at different longitudinal locations (see FIG. 3 for example). In such embodiments, a pair of slots and a single arch may be located at one particular longitudinal location while a sequentially located second pair of slots and another single arch that are helically arranged with a third pair of slots and another single arch.

In the retaining configuration such as shown in FIG. 2A, the arches 54 bend outward from a central axis of the retention scaffold 50. In a loading configuration as shown in FIG. 2B, the arches are aligned parallel with the central catheter. The two configurations, namely loading and retention configurations, are interchangeable by longitudinally displacing one end 84A relative to a second end 86A, such as when one end cannot be moved and a force is applied to the other end. Thus, when loading a stent graft onto the delivery device, an arch 54A or if there is more than one arch, the arches and slots 52A can be parallel to one another and to the central catheter or cannula 53 (not shown in FIGS. 2A and 2B). Following placement of the stent 60 in its compressed configuration onto retention scaffold 50A along the central catheter 53, one or both ends 84A and 86A are moved closer to one another thereby extending the arch 54A or arches through openings in the stent graft 60. For example, a stent graft 60 is placed over the central catheter 53 and retention scaffold 50, and force is applied to one end of the retention scaffold 50 thereby causing the arches 54 to bend outward through the stent graft 60.

Referring to FIG. 3, the arches 54 can extend through openings such as slots 62 in the stent struts 64 of the stent graft 60. Alternatively, the arches can extend through openings such as gaps 68 between stent struts 64. In some embodiments, the arches may extend through slots 62 and gaps 68 as may be desired for helical alignment.

The combination of the stent struts 64 and arches 54 create an aperture 56 through which a trigger wire 70 passes through. In some embodiments, such as shown in FIG. 3, the helical path of the trigger wire 70 occurs across various longitudinal locations along the retention scaffold. As shown in FIG. 3, the trigger wire 70 can helically wind through the apertures 56 to retain at least a portion of the stent graft 60 onto the delivery device even after withdrawal of the sheath 110. During deployment, the trigger wire 70 is withdrawn from each aperture allowing the self-expanding stent to expand into a deployed configuration. In the deployed confirmation, the stent graft 60 can engage with the patient's vessel wall, for example with barbs 66.

In some embodiments, such as shown in FIG. 4, the helical path of the trigger wire 70 occurs across the span 90 of apertures that are circumferentially located at a common longitudinal location.

One end of the trigger wire may releasably engage with the nose cone dilator 11, and the other end may be affixed to a trigger wire release device.

Referring to FIGS. 5A, 5B, 6A, and 6B, another retention scaffold and its components are shown. The retention scaffold includes a plurality of lateral struts 158, each having a first end 181 and a second end 183. The ends form loops 185 and 187 which can encircle a central catheter 153. The lateral struts are assembled onto the central catheter 153 by threading the catheter 153 through the first loop 185A of a first strut 154A, followed by the first loop 185B of a second strut 154B, the first loop 185C of a third strut 154C, the first loop 154D of a fourth strut 185D, the second loop 187A of the first strut 154A, the second loop 187B of the second strut 154B, the second loop 187C of the third strut 154C, and the second loop 187D of the fourth strut 154D. In this embodiment, four loops are presented by the retention scaffold. In other embodiments, the number of struts can be increased or decreased to accommodate more or fewer arches and apertures desired. The number of arches can range from 1-8 in some embodiments, and from 2-6 in some embodiments. The arches 154A-D form apertures 156A-D through which a trigger wire (not shown) may helically pass. It is desired that the trigger wire not circumferentially pass through the aperture but include a longitudinal displacement thereby following a helical path through the apertures.

Figure 7:
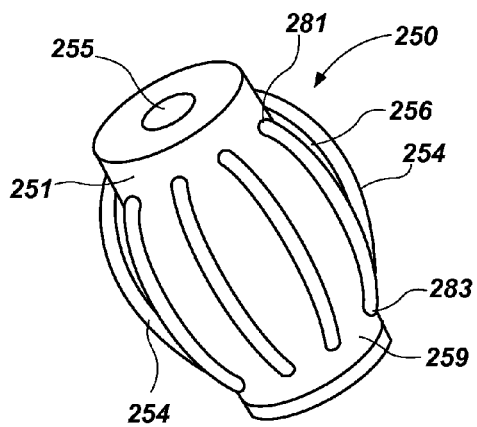
FIG. 7 depicts a perspective view of another embodiment of the invention without a central catheter.

In another embodiment depicted in FIG. 7, the retention scaffold 250 includes a cylindrical sleeve 251 with a passageway 255 through which a central catheter can pass. The retention scaffold has a plurality of arches 254 which can be soldered or otherwise adhered to cylindrical face 259 of the sleeve 251 at first and second ends 281 and 283 respectively. The number of arches 254 can be varied as desired. The arches 254 with the cylindrical sleeve 251 form apertures 256 through which a trigger wire (not shown) may helically pass.

Figure 8:
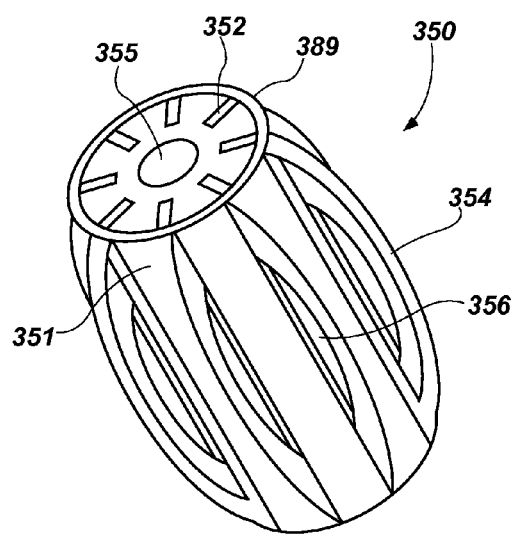
FIG. 8 depicts a perspective view of another embodiment of the invention without a central catheter.

In another embodiment depicted in FIG. 8, the retention scaffold 350 includes a cylindrical sleeve 351 with a passageway 355 through which a central catheter can pass. The retention scaffold 350 includes a plurality of slots 352. The slots can be filled with cleats 389 having arches 354 forming apertures 356. The cleats 389 can be soldered or otherwise adhered into the slots 352. The number of arches 354 can be varied as desired. A trigger wire (not shown) may helically pass through the apertures 356.

Figure 9A:
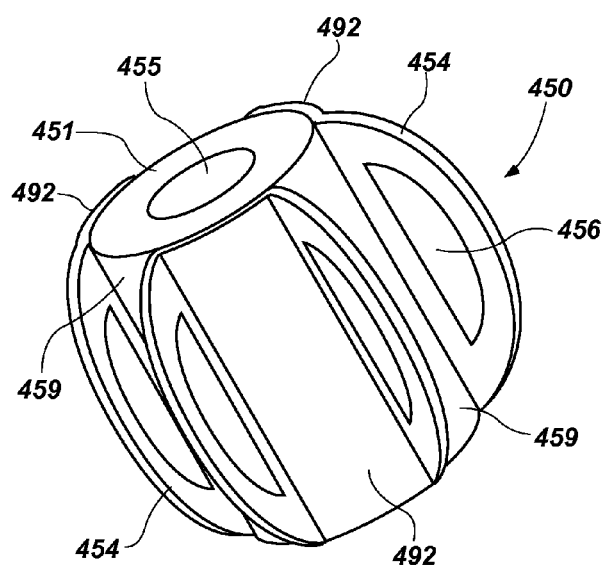
FIG. 9A depicts a perspective view of another embodiment of the invention without a central catheter.
Figure 9B:
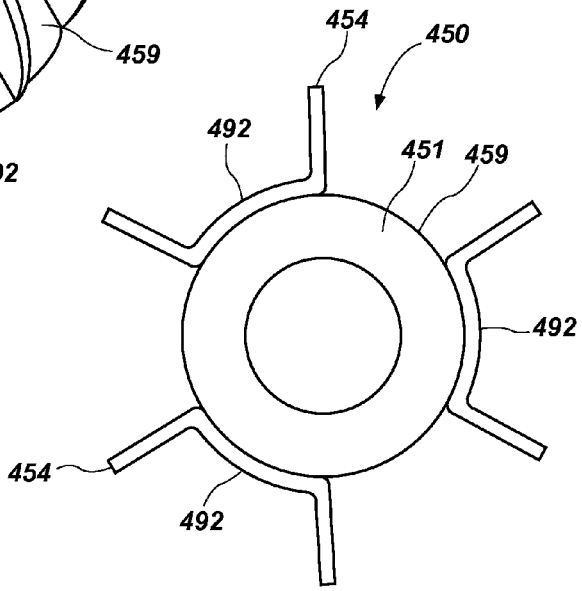
FIG. 9B depicts a top view of the embodiment of FIG. 9A without a central catheter.

In another embodiment depicted in FIGS. 9A and 9B, the retention scaffold 450 includes a cylindrical sleeve 451 with a passageway 455 through which a central catheter can pass. The retention scaffold 450 has a cylindrical face 459 to which a plurality of brackets 492 are connected. The brackets 492 may be soldered or otherwise adhered to the cylindrical face 459. In some embodiments, the brackets may be molded or cast integral with the cylindrical sleeve 451. The brackets 492 include at least one arch, such as a pair of arches 454 as shown in FIGS. 9A and 9B. The arches 454 with the brackets 492 form apertures 456 through which a trigger wire (not shown) may helically pass.

In some embodiments, each bracket may have a single arch. In some embodiments, each bracket may have a pair of arches. In some embodiments, each bracket may have three or more arches. In some embodiments, the brackets may be longitudinally offset from one another to further position the arches for a more defined helical path for a trigger wire. In some embodiments, an arch or arches on the brackets may be longitudinally offset from another arch or arches on other brackets to more define a helical path for a trigger wire.

With reference to FIG. 10, some embodiments of the retention scaffold may be augmented with a piloting end 595 configured to be connectable with a shaft end 598. The piloting end is located on a distal end a retention scaffold. The piloting end may have a recess 597 that can be connectable with a corresponding interlocking protrusion 596 on the shaft end 598. The interlocking feature can give the operator of the delivery device the ability to further maneuver the placement of the stent graft by facilitating longitudinal and rotational control of the retention scaffold 554 and, therefore, the stent graft itself. For example, an operator can longitudinally move a shaft 503 thereby longitudinally moving the retention scaffolding proximally. An operator can also apply torque to the shaft 503 thereby applying torque to the retention scaffold. The interlocking feature can be configured in a variety of configurations that enable the user to engage the piloting and shaft ends. For example, matching zigzag or teeth-like configurations and others known in the art may be used.

The retention scaffold of the various configurations described above may be may be located near or at one or both of the stent graft's openings. Additional retention scaffolds may be located in intermediate positions between the first and second openings of the stent graft. Generally speaking, if a metallic material is used, the central catheter or cannula is a cannula. If a more flexible material is used, the central catheter or cannula is a catheter.

The retention scaffold and central catheter may be made of any of a variety of materials, including nickel titanium alloys such as Nitinol® which is conducive to precision laser cutting. In some embodiments, one or both of the retention scaffold and central catheter may be made of polyether ether ketone material (PEEK).

In some embodiments, such as the one shown in FIG. 3, anchors or barbs 66 may be circumferentially located about the first end of a stent graft. The barbs may also be staggered at longitudinal locations along a stent graft. Radiopaque markers can be applied to the stent struts on the graft material. The markers can be used by the operator for positioning the stent graft.

In one aspect, a method of preparing a stent graft for delivery to a patient is disclosed. The method involves providing a central catheter and a retention scaffold. The retention scaffold has a plurality of arches that are bowed outward after a stent graft is overlaid on the retention scaffold with the arches passing through openings in the stent graft. The proximal-most stent strut of the stent graft has an arch with a first aperture. While the arches are held in position and the stent graft in a compressed configuration, the trigger wire is passed through each sequential aperture formed by the arches in a helical path around the stent graft until all desired apertures have been threaded with the trigger wire, and the trigger wire is immediately adjacent to the outer surface of the central catheter. The trigger wire can be then retracted to a control handle and trigger wire release mechanism.

In another aspect, a method of deploying a stent graft is disclosed. The method includes the step of inserting an introducer into a patient's body in a position adjacent to the treatment site. The treatment site can be any lumen or vessel location where a rupture, aneurysm, or location for repair is required. The sheath of the introducer is partially withdrawn to uncover the implant retained on the delivery device using a retention scaffold as described herein, and to assure that the position of the proximal end of the implant is at a desired location. A helically wound trigger wire retaining the stent graft with the retention scaffold is withdrawn allowing the self-expanding stent to expand radially in a controlled manner. Barbs or other anchors in the stent graft affix the graft to the desired location. The sheath may be further withdrawn to fully deploy the stent graft.

In various manufacturing method embodiments, the delivery device can be adapted and provided with the features as described above for the various physical embodiments.

Throughout this specification, various indications have been given as to the scope of this invention, but the invention is not limited to any one of these but may reside in two or more of these combined together. The examples are given for illustration only and not for limitation. Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. An endovascular delivery device, comprising:
    a central catheter;
    a stent graft circumferentially located about a portion of the central catheter, the stent graft comprising a tubular body of a biocompatible material with a lumen therethrough;
    a retention scaffold comprising a plurality of arches, each arch encompassing an aperture forming a helical path wherein the retention scaffold further comprises distal and proximal ends and the arches bow radially outward when one of the distal and proximal ends moves longitudinally toward the other one of the distal and proximal ends;
    a trigger wire passing through at least two of the apertures following the helical path, wherein at least a portion of the stent graft is retained in a compressed configuration on the delivery device by the retention scaffold and the trigger wire.

2. The delivery device of claim 1, wherein the stent graft comprises stent struts comprising openings and forming gaps between adjacent stent struts.

3. The delivery device of claim 2, wherein the arches extend through the stent strut openings.

4. The delivery device of claim 2, wherein the arches extend through the stent strut gaps.

5. The delivery device of claim 2, wherein the arches extend through the stent strut openings and the stent strut gaps.

6. The delivery device of claim 1, wherein the arches are helically located about the central catheter.

7. The delivery device of claim 1, wherein the retention scaffold is integral with the central catheter.

8. The delivery device of claim 1, wherein the retention scaffold is located circumferentially on the central catheter.

9. An endovascular delivery device, comprising:
    a central catheter;
    a shaft;
    a stent graft circumferentially located about a portion of the central catheter, the stent graft comprising a tubular body of a biocompatible material with a lumen therethrough;
    a retention scaffold comprising a proximal end and a piloting end and a plurality of arches, each arch encompassing an aperture forming a helical path wherein the retention scaffold further comprises distal and proximal ends and the arches bow radially outward when one of the distal and proximal ends moves longitudinally toward the other one of the distal and proximal ends, and wherein the piloting end interlocks with the shaft for rotating or longitudinally displacing a portion of the retention scaffold;
    a trigger wire passing through at least two of the apertures following the helical path, wherein the stent graft is retained in a compressed configuration on the delivery device by the retention scaffold and the trigger wire.

10. The delivery device of claim 9, wherein the stent graft comprises stent struts comprising openings and forming gaps between adjacent stent struts.

11. The delivery device of claim 10, wherein the arches extend through the stent strut openings.

12. The delivery device of claim 10, wherein the arches extend through the stent strut gaps.

13. The delivery device of claim 10, wherein the arches extend through the stent strut openings and the stent strut gaps.

14. The delivery device of claim 9, wherein the retention scaffold is integral with the central catheter.

15. A method of deploying a stent graft in a patient, comprising:
    providing an endovascular delivery device, comprising:
        a central catheter;
        a stent graft circumferentially located about the central catheter comprising a tubular body of a biocompatible material with a lumen therethrough;
        a retention scaffold comprising a plurality of arches, each arch encompassing an aperture forming a helical path herein the retention scaffold further comprises distal and proximal ends and the arches bow radially outward when one of the distal and proximal ends moves longitudinally toward the other one of the distal and proximal ends;
        a trigger wire passing through at least two of the apertures in the helical path, wherein the stent graft is retained in a compressed configuration on the delivery device by the retention scaffold and the trigger wire; and
    withdrawing the trigger wire through the apertures.

* * * * *